United States Patent [19]
Chopp et al.

[11] Patent Number: 5,305,751
[45] Date of Patent: Apr. 26, 1994

[54] MEASUREMENT OF LIQUID FLOWS IN A LIVING ORGANISM

[75] Inventors: Michael Chopp, Southfield; John Moran, Dearborn; Norman Tepley, Bloomfield Hills, all of Mich.

[73] Assignee: Biomagnetic Technologies, Inc., San Diego, Calif.

[21] Appl. No.: 893,503

[22] Filed: Jun. 4, 1992

[51] Int. Cl.$^5$ .............................................. A61B 5/026
[52] U.S. Cl. .................................... 128/654; 128/691
[58] Field of Search ..................... 128/653.1, 654, 691; 324/244, 248

[56] References Cited

U.S. PATENT DOCUMENTS 4,079,730 3/1978 Wikswo, Jr. et al. ........... 128/653.1

FOREIGN PATENT DOCUMENTS 0084933 3/1990 Japan ................................ 128/653.1

OTHER PUBLICATIONS

M. Chopp et al., "Biomagnetic Measurements Utilizing Ferrofluids," *Book of Abstracts of 8th International Conference on Biomagnetism*, Munster, pp. 313-315 (Aug. 18-24, 1991).

Primary Examiner—Ruth S. Smith
Attorney, Agent, or Firm—Gregory Garmong

[57] ABSTRACT

A method of measuring liquid flows in a living organism comprises the steps of applying an applied magnetic field to a living organism, introducing a time-varying quantity of a magnetizable fluid into a flow of liquid in the living organism, and measuring the variation in an induced magnetic field emanating from the living organism as a measure of the flow of the magnetizable fluid and the liquid within the living organism. The measurement of the induced magnetic field is preferably accomplished with at least two magnetic field sensors positioned at different locations relative to the living organism, whose outputs are detected with SQUID detectors. A cross correlation of the outputs of the magnetic field sensors permits the flow of liquid to be deduced as a function of time and location.

20 Claims, 2 Drawing Sheets

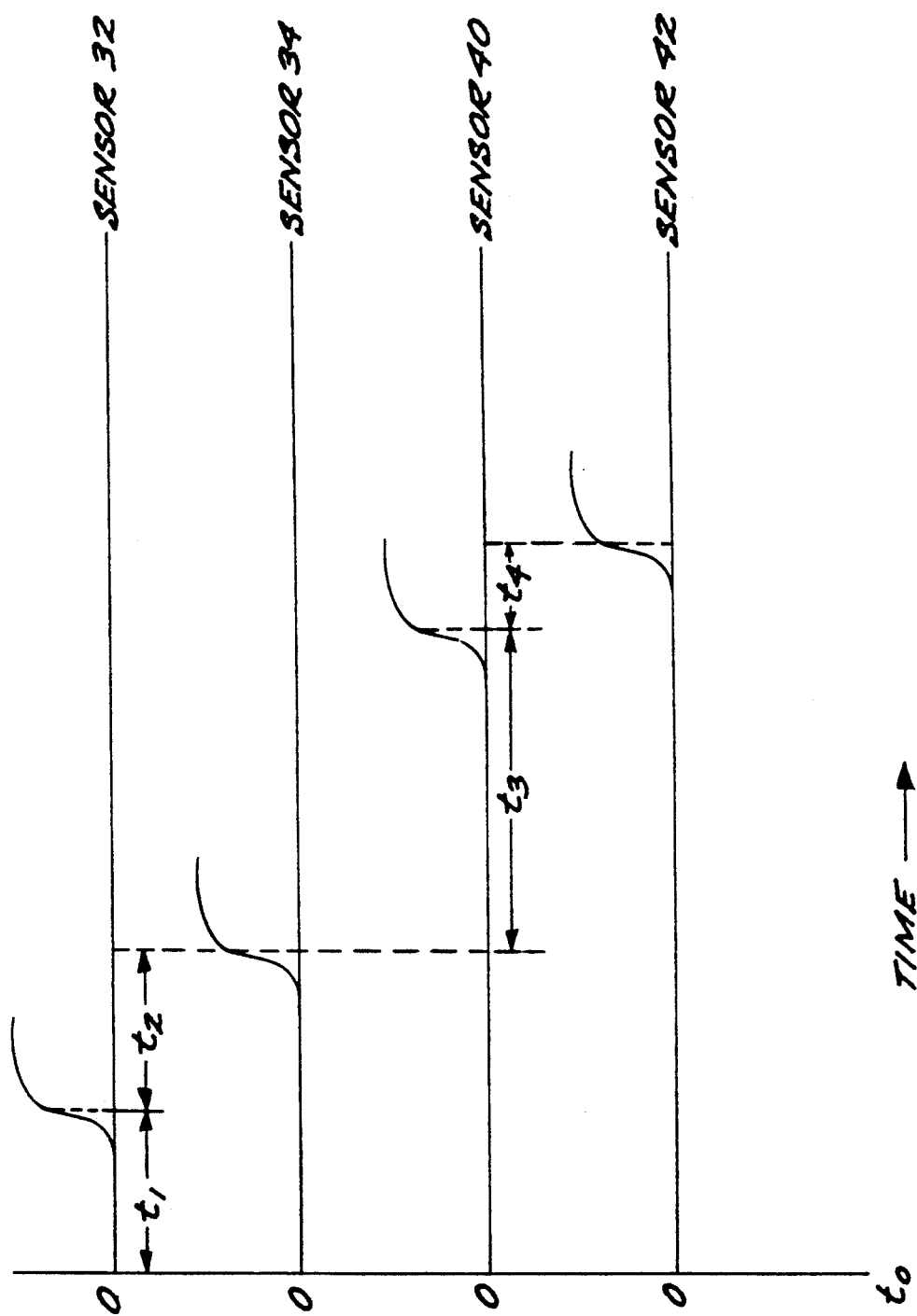

MEASUREMENT OF LIQUID FLOWS IN A LIVING ORGANISM

BACKGROUND OF THE INVENTION

The present invention relates to the measurement of liquid flow in a living organism, and, more particularly, to such measurements performed using magnetic field measurements.

The flow and circulation of liquids in the body of a living organism are an important aspect of the health of the organism. The principal liquid flowing in the body is blood, which carries nutrients and oxygen to cells and returns waste from the cells. Irregularities in the flow of blood through the heart and blood vessels indicate the presence of constrictions or malfunctions. The irregularities in blood flow in turn often lead to other problems.

Health care workers have long monitored the flow of blood in the body, and there are a variety of techniques that can be used for this purpose. A stethoscopic examination can determine some aspects of blood flow, but this approach is quite limited. Blood flow can be monitored by injecting X-ray absorbing dyes or radioactive tracers, followed by measurements of the progress of the dyes or tracers with X-rays or radioactivity counters, respectively. These approaches, while operable, have the disadvantage of low spatial resolution, possible destruction of cells, and, in some cases, the need to inject relatively large amounts of tracer material due to the relatively low sensitivity of the techniques.

There is therefore a need for an approach that permits monitoring the flow of liquids in the body which is of high sensitivity and which produces essentially no adverse side effects. The present invention fulfills this need, and further provides related advantages.

SUMMARY OF THE INVENTION

The present invention provides an approach for monitoring liquid flows through the body of a living organism such as a human being or an animal. Although the approach of the invention requires the introduction of a fluid into the body, the method has high sensitivity and therefore requires a minimal introduction of the fluid. The approach is operable for monitoring any liquid flow in the body, such as that of blood, urine, and injected liquids.

In accordance with the invention, a method of measuring liquid flows in a living organism comprises the steps of applying an applied magnetic field to a living organism, introducing a time-varying quantity of a magnetizable fluid into a flow of liquid in the living organism, and measuring the temporal or spatial variation in an induced magnetic field emanating from the living organism as a measure of the flow of the magnetizable fluid and the liquid within the living organism.

The magnetizable fluid is preferably a suspension of small magnetite particles in a carrier fluid. Such fluids are paramagnetic (also sometimes termed "superparamagnetic") and can be magnetized to exhibit an induced magnetic field of greater magnitude than the applied magnetizing field. Such fluids are available commercially.

A magnetizing field is applied to the living organism to be studied. The applied magnetizing field may be constant or varying in time or spatially varying, as may be appropriate to the variation of the technique to be used. A small quantity of the magnetizable fluid is introduced into the liquid to be studied, diluting the magnetizable fluid in that liquid. The amount of the magnetizable fluid injected varies as a function of time, either by changing the amount of the magnetizable component of the fluid or the total amount of introduced fluid, as a function of time. For example, if the flow of blood in a particular region of a leg is to be studied, a small quantity of the magnetizable fluid is injected into an artery leading to that region. The magnetizing field applied to the body induces an induced magnetic field in the magnetizable fluid as it flows through the blood vessels. Although conceivably it would not be necessary to apply a magnetic field to the magnetizable fluid due to the presence of the earth's magnetic field, the present invention requires the use of an applied magnetic field to induce magnetism in the flowing magnetizable fluid.

The progress of the magnetizable fluid through the blood vessels is preferably measured externally to the body by a biomagnetometer. This instrument includes one or more, usually a plurality of, magnetic field sensors such as single-loop magnetometers or gradiometers. Passage of a time-varying induced magnetic field through the sensor produces an electrical current, which in turn is detected by a sensitive electrical detector. Present biomagnetometers utilize Superconducting QUantum Interference Device ("SQUID") detectors coupled to the magnetic field sensors to detect the small currents resulting from very small magnetic field fluxes.

Magnetic field sensor/SQUID detector combinations are highly sensitive to magnetic field variations. They can therefore record the movement of the magnetizable fluid in the living organism, even when the concentration of the magnetizable fluid in the organism is very low. The geometry of the sensor system can be varied depending upon the nature of the study being performed. However, typically there would be several sensors and associated SQUIDs at varying locations selected so that the passage of the magnetizable fluid through the region can be monitored from the sensed induced magnetic field changes.

The present invention provides an advance in the field of monitoring liquid flows in living organisms. Other features and advantages of the invention will be apparent from the following more detailed description of the invention, taken in conjunction with the accompanying drawings, which illustrate, by way of example, the principles of the invention.

BRIEF DESCRIPTION OF THE DRAWINGS

FIG. 2 is a graphical superimposition of the induced magnetic field outputs of four SQUID detectors as a function of time.

DETAILED DESCRIPTION OF THE INVENTION

Figure 1:
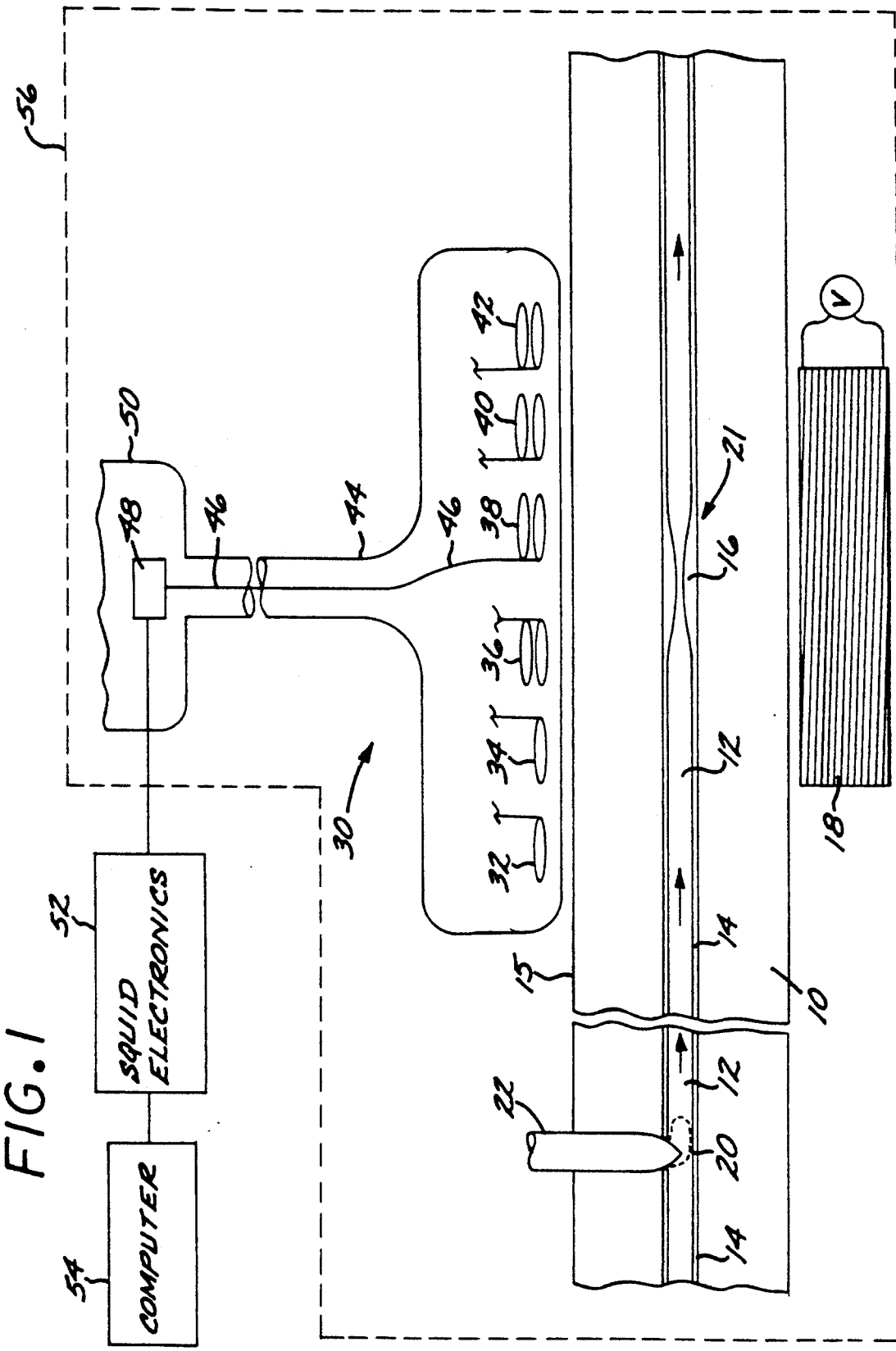
FIG. 1 is a schematic view of an arrangement to practice the present invention.

FIG. 1 schematically depicts the practice of the present invention as used to measure blood flow in a human body 10 and identify and locate impediments to that blood flow. The blood 12 flows through a blood vessel 14 that is below a surface 15 of the body 10. To illustrate the use of the invention, it is assumed that the blood vessel 14 is of generally constant internal cross-sectional area over most of its length, but has an internal constriction 16 over a portion of its length.

In accordance with a preferred embodiment of the invention, an applied magnetic field is applied to the body 10 by a magnet 18 positioned externally to the body. The magnet 18 may be a permanent magnet that produces a constant applied magnetic field, or, as depicted, an electromagnet that can produce either a constant applied magnetic field or a time-varying applied magnetic field.

A time-varying quantity of a magnetizable fluid 20 is introduced into the blood 12 in the blood vessel 14 at a location remote from a measurement region of interest 21, through a needle 22. The magnetizable fluid mixes with the blood (or other liquid in the body) and flows along with the blood. The needle 22 is preferably placed at a distance upstream from the measurement region of interest 21 sufficiently far that the magnetizable fluid is uniformly distributed across the width of the blood vessel 14 by the time that it reaches the region of interest 21. Also, displacement of the point of introduction upstream reduces the magnetic interference of the injection on the magnetic field measurements.

The magnetizable fluid is preferably a paramagnetic ferrofluid consisting of a suspension of 100 Angstrom diameter magnetite particles in water, stabilized with an anionic surface active agent. Such a fluid is available as Ferrofluid Type EMG507 from Ferrofluidics Corp., Nashua, N.H. This particular magnetizable fluid is superparamagnetic with a magnetic susceptibility of 0.5 to 5, saturates at an applied magnetic field of 100–400 Gauss, and exhibits no magnetic hysteresis.

A flow of blood, because it contains iron, exhibits a small magnetic field even without the presence of the magnetizable fluid. A flow of the magnetizable fluid also exhibits a small magnetic field even without the application of a magnetic field by the magnet 18. However, these fields are so small that they are not practically utilized for measurements of liquid flows in the living organism, unless a very high concentration of the magnetizable fluid is used. The present invention provides that the magnetizable fluid is induced to exhibit a higher induced magnetic field as a result of the applied magnetic field of the magnet 18. The higher induced magnetic field makes measurements of the liquid flow in the body practical with very small additions of the magnetizable fluid, which in turn do not produce substantial side effects and permit extended studies.

When a time-varying quantity of a magnetizable fluid moves through an applied magnetic field, a varying current and thence a varying induced magnetic field results. The varying induced magnetic field is detected and measured by a biomagnetometer 30 positioned externally to the body. The time variations in the induced magnetic field sensed by the various sensors of the biomagnetometer 30, and a cross correlation of the signals produced by the various sensors leads to an understanding of the environment through which the magnetizable fluid is moving.

(There are two magnetic fields involved in the present invention, and must be carefully distinguished. The applied magnetic field is created within the region of interest 21 by the operation of the magnet 18. The induced magnetic field is that which results from the presence and movement of the magnetizable fluid in the region of interest 21, and is measured externally by the biomagnetometer 30.)

Biomagnetometers suitable to the practice of the present invention are available commercially from Biomagnetic Technologies, Inc., San Diego, Calif. The structure and operation of such biomagnetometers are well known to those skilled in the art. FIG. 1 depicts a biomagnetometer that has been adapted to be particularly useful in measurements of liquid flows in living organisms. This biomagnetometer is preferably of the type disclosed in U.S. Pat. No. 5,061,680, whose disclosure is incorporated by reference, although more conventional biomagnetometers can also be used.

This biomagnetometer 30 includes at least two, and typically a plurality, of magnetic field sensors, here indicated as sensors 32, 34, 36, 38, 40, and 42. The sensors are distributed through space in an arrangement selected to yield the required information. In the case of an investigation of blood flow through a blood vessel 14, the sensors are typically arranged along the length of the blood vessel, as illustrated. The use of the present invention is not limited to measurements of a blood flow in a long blood vessel lying near the surface of the body, which is used in the illustration for convenience. Movement of blood in deeply buried vessels can be measured, as for example blood vessels within the brain and within organs such as the heart.

Each sensor includes a pickup coil that may be a planar-loop magnetometer, such as illustrated for the sensors 32 and 34, or a three-dimensional gradiometer, such as illustrated for the sensors 36, 38, 40, and 42. In each case, when magnetic flux penetrate the sensor, an electrical current is produced. The electrical current is typically very small, because the concentration of the magnetizable fluid 20 is selected to be as small as possible to avoid side effects. The resulting induced magnetic fields are small, on the order of less than 10,000 femtotesla.

In the biomagnetometer constructed in accordance with the '680 patent, the sensors 32, 34, 36, 38, 40, and 42 are made of a superconductor and are placed in an insulated enclosure 44 that is filled with a cryogenic coolant appropriate to the superconductor, such as liquid nitrogen or liquid helium, to maintain the sensors in the superconducting state. Loss of current due to electrical resistance is thereby avoided. The respective signal of each of the sensors is conveyed through a lead 46 to a superconducting quantum interference device ("SQUID") 48. (In FIG. 1 only a single lead and SQUID are shown to reduce clutter in the drawing, but in practice there is typically a dedicated lead system and SQUID for each of the sensors.) The SQUID 48 may be placed in the same container as its sensor, or, as shown, may be placed in another insulated container 50 filled with a cryogenic gas. The advantage of placement of the SQUID in a separate container is that the container 50 may be maintained at a lower cryogenic temperature than the container 44, such as at liquid helium temperature, to improve the electronic performance of the SQUID 48.

The SQUID 48 detects the small electrical current flow produced when a magnetic flux penetrates the sensor 40, and produces an output signal. That output signal is transmitted to conventional ambient-temperature SQUID electronics 52, and the output of the SQUID electronics 52 is gathered, stored, and processed by a microcomputer 54. SQUID design and electronics are well known in the art, and are described, for example, in U.S. Pat. Nos. 4,386,361, 4,403,189, 3,980,076, and 4,079,730, whose disclosures are incorporated by reference.

The data acquired from the sensors may then be processed by processing techniques available in the art, such as the approach disclosed in U.S. Pat. No. 4,977,896, whose disclosure is incorporated by reference. To improve the signal-to-noise ratio of the results, the living organism under study, the magnet, the sensors, and the SQUID detectors may be placed in a magnetically shielded room 56, indicated schematically in FIG. 1. Such magnetically shielded rooms are disclosed, for example, in U.S. Pat. Nos. 3,557,777 and 5,043,529, whose disclosures are incorporated by reference.

FIG. 2 illustrates the type of results that would be produced by the arrangement of FIG. 1, when operating in the manner discussed previously. The magnetizable fluid 20 is injected through the needle 22 at a time t0, and flows through the blood vessel 14 from left to right in the drawing of FIG. 1. At a time t1 after introduction of the magnetizable fluid, sensor 32 detects the increased induced magnetic field produced by the leading edge of the flow of the magnetizable fluid. Sensor 34 detects the leading edge of the flow of the magnetizable fluid a short time t2 later. Sensor 40 detects the leading edge at a time t3 later (this discussion omits sensors 36 and 38, but they would show similar patterns), and sensor 42 detects the leading edge at a time t4 later. The presence of the constriction 16 restricts the total flow rate (volume per unit time) of blood in the blood vessel 14 to the same value at all locations. However, the velocity of flow (distance per unit time) varies as a function of position. Upstream of the constriction 16 the flow velocity is relatively slow, and downstream of the constriction 16 the flow velocity is relatively faster. Accordingly, the time t4 is less than the time t2 (assuming that the sensors are equally spaced for this example). Moreover, the faster flow past the sensors 40 and 42 produces an induced magnetic field of greater magnitude than the slower flow past the sensors 32 and 34. Thus, two aspects of the measurement of the sets of sensors permits one to deduce the presence of the constriction 16 in the blood vessel 14, somewhere between the sets of sensors.

The operability of the present approach has been verified by measurements of an anesthetized rat. The study was performed in a magnetically shielded room using a Model 607 biomagnetometer available from Biomagnetic Technologies, Inc. and with an applied magnetic field of the magnet 18 of about 0.2 microtesla. For this feasibility study the instrument had a non-optimized circular array of seven second-order gradiometers, not the linear array of FIG. 1.

The right femoral vein of the rat was cannulated for an infusion of ferrofluid. Magnetic data was collected for 30 seconds, after which 0.3 cc (cubic centimeters) of diluted magnetizable fluid having a particle concentration of 0.085 volume percent was injected. Measurement signals generally similar to those depicted in FIG. 2 were obtained. The signals of the seven sensors were cross correlated, and showed that the flow rate of the magnetizable fluid and the blood was consistent with the flow pattern of blood through the body of the rat. To reach more quantitative conclusions would require optimization of the sensor coil arrangement, as shown in FIG. 1. The injection of magnetizable fluid was repeated three times, except that in the three subsequent injections a smaller amount, about 0.1 cc. of the same particle concentration magnetizable fluid was used. These subsequent injections proved that the concentration of the magnetizable fluid could be made quite small, and also that the results were repeatable. After the study was complete, the cannula was removed and the rat returned to its cage. The rat suffered no seizures or other apparent abnormalities resulting from the procedure.

The present invention provides an apparatus and method for determining the flow of liquids within a living organism. Although particular embodiments of the invention have been described in detail for purposes of illustration, various modifications may be made without departing from the spirit and scope of the invention. Accordingly, the invention is not to be limited except as by the appended claims.

What is claimed is:

1. A method of measuring liquid flows in a living organism, comprising the steps of:
    applying an applied magnetic field to a living organism;
    introducing a quantity of a magnetizable fluid from an external source into a flow or liquid in the living organism, wherein the quantity of magnetizable liquid flowing from the external source varies as a function of time; and
    measuring the variation in an induced magnetic field emanating from the living organism as a measure of the flow of the magnetizable fluid and the liquid within the living organism, the step of measuring including a step of determining a liquid flow from the measured magnetic field variation.

2. The method of claim 1, wherein a constant applied magnetic field is applied during the step of applying.

3. The method of claim 1, wherein a time-varying applied magnetic field is applied during the step of applying.

4. The method of claim 1, wherein a spatially varying applied magnetic field is applied during the step of applying.

5. The method of claim 1, wherein the step of introducing includes the step of
    providing a magnetizable fluid which exhibits paramagnetism.

6. The method of claim 1, wherein the step of introducing includes the step of
    providing a magnetizable fluid which is a suspension of magnetite particles in a carrier fluid.

7. The method of claim 1, wherein the step of measuring includes the substeps of
    positioning at least two magnetic field sensors at different locations adjacent to the living organism, and
    determining the induced magnetic field as a function of time at each of the magnetic field sensors.

8. The method of claim 7, including the additional step, after the step of determining, of
    correlating the induced magnetic fields sensed by each of the magnetic field sensors to deduce the flow of the magnetizable fluid past the magnetic field sensors.

9. The method of claim 1. wherein the living organism is a human being.

10. The method of claim 1, wherein the living organism is a non-human animal.

11. A method of measuring liquid flows in a living organism, comprising the steps of:
    applying an applied magnetic field to a living organism;
    introducing a quantity of a magnetizable fluid from an external source into a flow of liquid in the living organism, wherein the quantity of magnetizable fluid flowing from the external source varies as a function of time;

measuring the variation in an induced magnetic field emanating from the living organism as a measure of the flow of the magnetizable fluid and the liquid within the living organism using at least two magnetic field sensors disposed adjacent to the body, each magnetic field sensor having an associated SQUID detector that detects the electric current flowing in its associated magnetic field sensor; and correlating the induced magnetic fields sensed by each of the magnetic field sensors to deduce the flow of the magnetizable fluid past the magnetic field sensors.

12. The method of claim 11, wherein a constant applied magnetic field is applied during the step of applying.

13. The method of claim 11, wherein a time-varying applied magnetic field is applied during the step of applying.

14. The method of claim 11, wherein a spatially varying applied magnetic field is applied during the step of applying.

15. The method of claim 11, wherein the step of introducing includes the step of providing a magnetizable fluid which exhibits paramagnetism.

16. The method of claim 11, wherein the step of introducing includes the step of providing a magnetizable fluid which is a suspension of magnetite particles in a carrier fluid.

17. The method of claim 11, wherein the step of measuring includes the step of providing magnetic field sensors which are made of a material that is a superconductor when cooled below a superconducting transition temperature.

18. The method of claim 11, wherein the step of measuring includes the step of providing magnetic field sensors which are planar loop magnetometers.

19. The method of claim 11, wherein the step of measuring includes the step of providing magnetic field sensors which are gradiometers.

20. The method of claim 11, wherein the step of correlating includes the step of determining the flow rate of the liquid.

* * * * *